US006730188B2

(12) United States Patent
Sanders

(10) Patent No.: US 6,730,188 B2
(45) Date of Patent: May 4, 2004

(54) METHOD AND APPARATUS FOR ASSEMBLING REFASTENABLE ABSORBENT GARMENTS

(75) Inventor: Donald J. Sanders, Larsen, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 228 days.

(21) Appl. No.: 09/954,478

(22) Filed: Sep. 14, 2001

(65) Prior Publication Data

US 2003/0051803 A1 Mar. 20, 2003

(51) Int. Cl.$^7$ ............................................. B32B 31/00
(52) U.S. Cl. ...................... 156/256; 156/200; 156/204; 156/226; 156/227; 156/265; 156/270; 156/302; 156/301; 156/518; 156/519; 156/520; 156/522; 156/461; 156/465
(58) Field of Search .................... 156/200, 204, 156/226, 227, 264, 302, 301, 73.1, 461, 465, 519, 518, 520, 265, 270, 522

(56) References Cited

U.S. PATENT DOCUMENTS

| 3,663,962 A | 5/1972 | Burger |
| 3,828,367 A | 8/1974 | Bourgeois |

(List continued on next page.)

FOREIGN PATENT DOCUMENTS

| DE | 198 13 334 A1 | 9/1999 |
| EP | 0 396 512 A2 | 11/1990 |

(List continued on next page.)

OTHER PUBLICATIONS

International Search Report for PCT/US02/12548, mailed Oct. 29, 2002.

U.S. patent application Ser. No. 09/002,020, entitled "Personal Care Article Having a Stretch Outer Cover and Non-Stretch Grasping Panels," filed Dec. 31, 1997 (KC 12,221).

(List continued on next page.)

Primary Examiner—Linda Gray
(74) Attorney, Agent, or Firm—Brinks Hofer Gilson & Lione

(57) ABSTRACT

A method for fabricating a refastenable absorbent garment comprises moving a continuous absorbent garment subassembly in a machine direction, wherein the continuous absorbent garment subassembly comprises a continuous front body panel web, a continuous rear body panel web and a plurality of discrete crotch portions spaced along the machine direction and connecting the continuous front and rear body panel webs. The crotch portions are folded in a cross direction with one of the continuous front and rear body panel webs folded over the other of the continuous front and rear body panel webs in the cross direction. The method further comprises successively cutting the continuous front and rear body panels of the continuous absorbent garment subassembly in the cross direction and thereby forming a plurality of discrete absorbent garment subassemblies, each of which comprises a front body panel and a rear body panel, wherein the front and rear body panels are connected with the crotch portion. Each of the front and rear body panels have opposite side edges, wherein the side edges form the leading and trailing edges of the discrete absorbent garment subassemblies in the machine direction. The method further includes successively rotating each of the discrete absorbent garment subassemblies such that the side edges are spaced apart in the cross direction. The method further comprises attaching a fastener member to at least one of the front and rear body panels on each of the discrete absorbent garment subassemblies. An apparatus for fabricating a refastenable absorbent garment includes a product rotator, at least one vacuum conveyor positioned downstream of the product rotator and a fastener applicator positioned downstream of the at least one vacuum conveyor.

31 Claims, 3 Drawing Sheets

U.S. PATENT DOCUMENTS

| | | | |
|---|---|---|---|
| 3,874,032 A | 4/1975 | Simon et al. |
| 4,409,052 A | 10/1983 | von Agris et al. |
| 4,608,115 A | 8/1986 | Schroth et al. |
| 4,615,695 A | 10/1986 | Cooper |
| 4,647,336 A | 3/1987 | Coenen et al. |
| 4,650,530 A | 3/1987 | Mahoney et al. |
| D290,780 S | 7/1987 | Wistrand |
| 4,713,132 A | 12/1987 | Abel et al. |
| 4,743,241 A | 5/1988 | Igaue et al. |
| 4,758,293 A | 7/1988 | Samida |
| 4,801,298 A | 1/1989 | Sorenson et al. |
| 4,847,134 A | 7/1989 | Fahrenkrug et al. |
| 4,906,243 A | 3/1990 | Dravland |
| 4,960,414 A | 10/1990 | Meyer |
| 4,998,929 A | 3/1991 | Bjorksund et al. |
| 5,080,741 A | 1/1992 | Nomura et al. |
| 5,087,253 A | 2/1992 | Cooper |
| 5,096,532 A | 3/1992 | Neuwirth et al. |
| 5,110,403 A | 5/1992 | Ehlert |
| 5,145,351 A | 9/1992 | Rossi |
| 5,147,487 A | 9/1992 | Nomura et al. |
| 5,221,390 A | 6/1993 | Persson et al. |
| 5,235,515 A | 8/1993 | Ungpiyakul et al. |
| 5,242,436 A | 9/1993 | Weil et al. |
| 5,286,543 A | 2/1994 | Ungpiyakul et al. |
| 5,340,424 A | 8/1994 | Matsushita |
| 5,370,634 A | 12/1994 | Ando et al. |
| 5,376,198 A | 12/1994 | Fahrenkrug et al. |
| 5,415,649 A | 5/1995 | Watanabe et al. |
| 5,449,353 A | 9/1995 | Watanabe et al. |
| 5,454,803 A | 10/1995 | Sageser et al. |
| 5,500,063 A | 3/1996 | Jessup |
| 5,540,796 A | 7/1996 | Fries |
| 5,542,943 A | 8/1996 | Sageser |
| 5,552,007 A | 9/1996 | Rajala et al. |
| 5,552,013 A | 9/1996 | Ehlert et al. |
| 5,554,145 A | 9/1996 | Roe et al. |
| 5,556,504 A | 9/1996 | Rajala et al. |
| 5,562,790 A | 10/1996 | Ehlert et al. |
| 5,569,234 A | 10/1996 | Buell et al. |
| 5,582,606 A | 12/1996 | Bruemmer et al. |
| 5,591,155 A | 1/1997 | Nishikawa et al. |
| 5,601,547 A | 2/1997 | Kato et al. |
| 5,609,702 A | 3/1997 | Andersen |
| 5,624,420 A | 4/1997 | Bridges et al. |
| 5,643,377 A | 7/1997 | Juergens |
| 5,643,396 A | 7/1997 | Rajala et al. |
| 5,659,229 A | 8/1997 | Rajala |
| 5,660,657 A | 8/1997 | Rajala et al. |
| 5,660,679 A | 8/1997 | Rajala et al. |
| 5,667,608 A | 9/1997 | Rajala et al. |
| 5,683,376 A | 11/1997 | Kato et al. |
| 5,685,873 A | 11/1997 | Bruemmer |
| 5,685,874 A | 11/1997 | Buell et al. |
| RE35,687 E | 12/1997 | Igaue et al. |
| 5,707,364 A | 1/1998 | Coates |
| 5,707,470 A | 1/1998 | Rajala et al. |
| 5,711,832 A | 1/1998 | Glaug et al. |
| 5,711,847 A | 1/1998 | Rajala et al. |
| 5,716,478 A | 2/1998 | Boothe et al. |
| 5,733,411 A | 3/1998 | Bett |
| 5,745,922 A | 5/1998 | Rajala et al. |
| 5,749,866 A | 5/1998 | Roe et al. |
| 5,749,989 A | 5/1998 | Linman et al. |
| 5,759,340 A | 6/1998 | Boothe et al. |
| 5,766,389 A | 6/1998 | Brandon et al. |
| 5,788,797 A | 8/1998 | Herrin et al. |
| 5,817,199 A | 10/1998 | Brennecke et al. |
| 5,836,931 A | 11/1998 | Toyoda et al. |
| 5,855,574 A | 1/1999 | Kling et al. |
| 5,858,151 A | 1/1999 | Igaue et al. |
| 5,858,515 A | 1/1999 | Stokes et al. |
| 5,879,500 A | 3/1999 | Herrin et al. |
| 5,897,545 A | 4/1999 | Kline et al. |
| 5,904,673 A | 5/1999 | Roe et al. |
| 5,940,887 A | 8/1999 | Rajala et al. |
| 5,957,908 A | 9/1999 | Kline et al. |
| 6,022,431 A | 2/2000 | Blenke et al. |
| 6,022,432 A | 2/2000 | Elsberg et al. |
| 6,036,805 A | 3/2000 | McNichols |
| 6,077,379 A | 6/2000 | Herrin et al. |
| 6,098,203 A | 8/2000 | Rajala et al. |
| 6,113,717 A | 9/2000 | Vogt et al. |
| 6,132,410 A | 10/2000 | Van Gompel et al. |
| 6,132,411 A | 10/2000 | Huber et al. |
| 6,139,004 A | 10/2000 | Couillard et al. |
| 6,197,138 B1 | 3/2001 | McNichols |
| 6,210,388 B1 | 4/2001 | Widlund et al. |
| 6,217,563 B1 | 4/2001 | Van Gompel et al. |
| 6,217,690 B1 | 4/2001 | Rajala et al. |
| 6,227,541 B1 | 5/2001 | Couillard et al. |
| 6,240,569 B1 | 6/2001 | Van Gompel et al. |
| 6,264,641 B1 | 7/2001 | Van Gompel et al. |
| 6,277,223 B1 | 8/2001 | Herrin et al. |
| 6,328,725 B2 | 12/2001 | Fernfors |
| 6,336,922 B1 | 1/2002 | Van Gompel et al. |
| 6,361,527 B1 | 3/2002 | Van Gompel et al. |
| 6,375,646 B1 | 4/2002 | Widlund et al. |
| 6,478,786 B1 | 11/2002 | Glaug et al. |
| 2001/0014798 A1 | 8/2001 | Fernfors |

FOREIGN PATENT DOCUMENTS

| | | |
|---|---|---|
| EP | 0528 282 A2 | 2/1993 |
| EP | 0 570 980 | 11/1993 |
| EP | 0 591 647 B1 | 4/1994 |
| EP | 0 630 221 B2 | 12/1994 |
| EP | 0 719 534 B1 | 7/1996 |
| EP | 1 062 930 A2 | 12/2000 |
| EP | 1 066 811 | 1/2001 |
| EP | 0 907 510 B1 | 3/2002 |
| GB | 2 288 316 | 11/1997 |
| GB | 2 311 249 | 7/1999 |
| JP | 03176053 A | 7/1991 |
| JP | 3-205053 | 9/1991 |
| JP | 4-22359 | 1/1992 |
| WO | WO 95/22306 | 8/1995 |
| WO | WO 95/27461 | 10/1995 |
| WO | WO 95/27462 | 10/1995 |
| WO | WO 96/14039 | 5/1996 |
| WO | WO 96/23466 | 8/1996 |
| WO | WO 96/23467 | 8/1996 |
| WO | WO 96/38112 | 12/1996 |
| WO | WO 97/02795 | 1/1997 |
| WO | WO 97/02797 | 1/1997 |
| WO | WO 97/02799 | 1/1997 |
| WO | WO 97/23180 | 7/1997 |
| WO | WO 97/46197 | 12/1997 |
| WO | WO 97/48357 | 12/1997 |
| WO | WO 98/27921 | 7/1998 |
| WO | WO 99/33425 | 7/1999 |
| WO | WO 00 20208 | 4/2000 |
| WO | WO 00/37009 | 6/2000 |
| WO | WO 01/13843 | 3/2001 |
| WO | WO 01/13844 | 3/2001 |
| WO | WO 01/13845 | 3/2001 |
| WO | WO 01/13846 | 3/2001 |
| WO | WO 01/13847 | 3/2001 |
| WO | WO 01/13848 | 3/2001 |
| WO | WO 01/13849 | 3/2001 |
| WO | WO 01/13850 | 3/2001 |
| WO | WO 01/13851 | 3/2001 |

OTHER PUBLICATIONS

U.S. patent application Ser. No. 09/954,506 "Method and Apparatus for Assembling Refastenable Absorbent Garments," filed on Sep. 14, 2001 (659–877).

U.S. patent application Ser. No. 09/954,444 entitled "Method and Apparatus for Assembling Refastenable Absorbent Garments," filed Sep. 14, 2001 (659–876).

U.S. patent application Ser. No. 09/954,480 entitled "Method and Apparatus for Assembling Refastenable Absorbent Garments," filed Sep. 14, 2001 (659–878).

U.S. patent application Ser. No. 09/637,432 entitled "Refastenable Absorbent Article Exhibiting Improved Body Fit," filed on Aug. 11, 2000 (KC 16098).

U.S. patent application Ser. No. 09/637,430 entitled "Refastenable Absorbent Article Exhibiting Improved Body Fit," filed Aug. 11, 2000 (KC 10699).

U.S. patent application Ser. No. 09/637,431 entitled "Refastenable Absorbent Article Exhibiting Improved Body Fit," filed Aug. 11, 2000 (KC 16100).

U.S. patent application Ser. No. 09/637,429 entitled "Absorbent Article Having a Refastenable Mechanism," filed Aug. 11, 2000 (KC 16101).

U.S. patent application Ser. No. 09/637,428 entitled "Absorbent Article Having a Refastenable Machanism," filed Aug. 11, 2000 (KC 16102).

U.S. patent application Ser. No. 09/637,427 entitled "Absorbent Article Having a Refastenable Mechanism," filed Aug. 11, 2000 (KC 16103).

U.S. patent application Ser. No. 09/637,423 entitled Absorbent Article Having a Refastenable Mechanism, filed Aug. 11, 2000 (KC 16104).

U.S. patent application Ser. No. 09/637,424 entitled "Absorbent Article Having a Refastenable Mechanism," filed Aug. 11, 2000 (KC 16105).

U.S. patent application Ser. No. 09/637,425 entitled "Absorbent Article Having a Refastenable Mechanism," filed Aug. 11, 2000 (KC 16106).

U.S. patent application Ser. No. 09/637,426 entitled "Absorbent Article Exhibiting Improved Body Fit," filed Aug. 11, 2000 (KC 16107).

U.S. patent application entitled "Methods of Changing Size of Pant–Type Personal Care Articles Outputted From a Manufacturing Process," filed Apr. 13, 2001 (KC 14755).

U.S. patent application Ser. No. 09/834,869 entitled "Pant-Type Personal Care Articles, and Methods of Making and Using Such Personal Care Articles," filed Apr. 13, 2001 (KC 14754).

U.S. patent application Ser. No. 09/834,682 entitled "Passive Bonds for Personal Care Article," filed Apr. 13, 2001 (KC15412).

U.S. patent application Ser. No. 09/834,870 entitled "Multiple Component Web," filed Apr. 13, 2001 (KC 15649).

U.S. patent application Ser. No. 09/834,875 entitled "Method of Assembling Personal Care Absorbent Article," filed Apr. 13, 2001 (KC 15490).

U.S. Provisional patent application Ser. No. 60/150,382 entitled "Pants, Refastenable Pants/Undergarments/Briefs Product Design and Process for Manufacturing on a Single Asset," filed Aug. 23, 1999 (KC 14509).

U.S. Provisional patent application Ser. No. 60/150,327 entitled "Refastenable Pant with Perforated Front Panels," filed Aug. 23, 1999 (KC 14647).

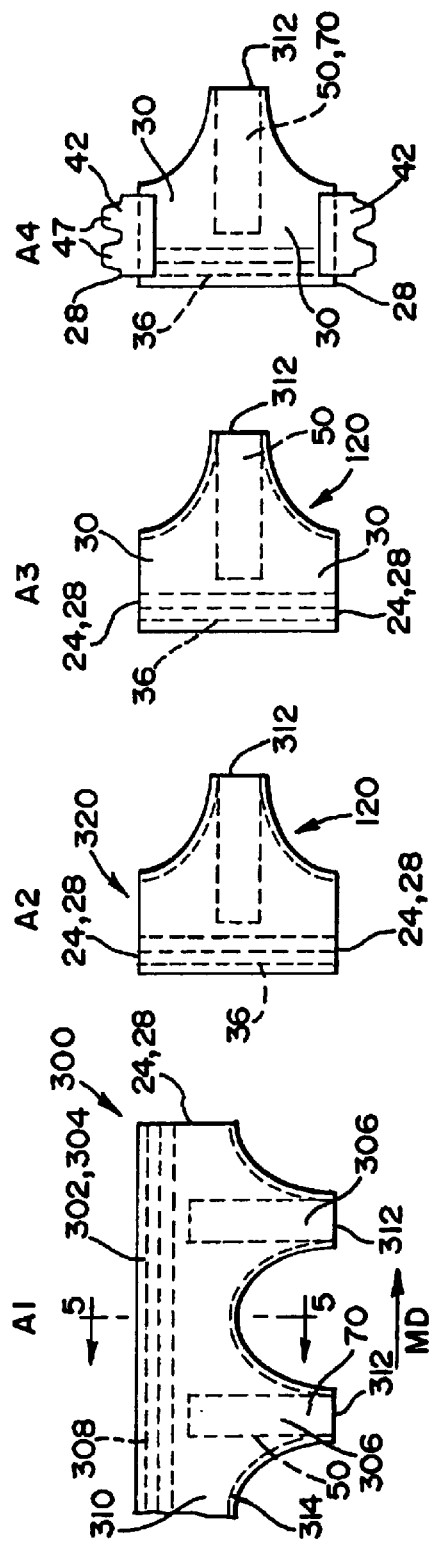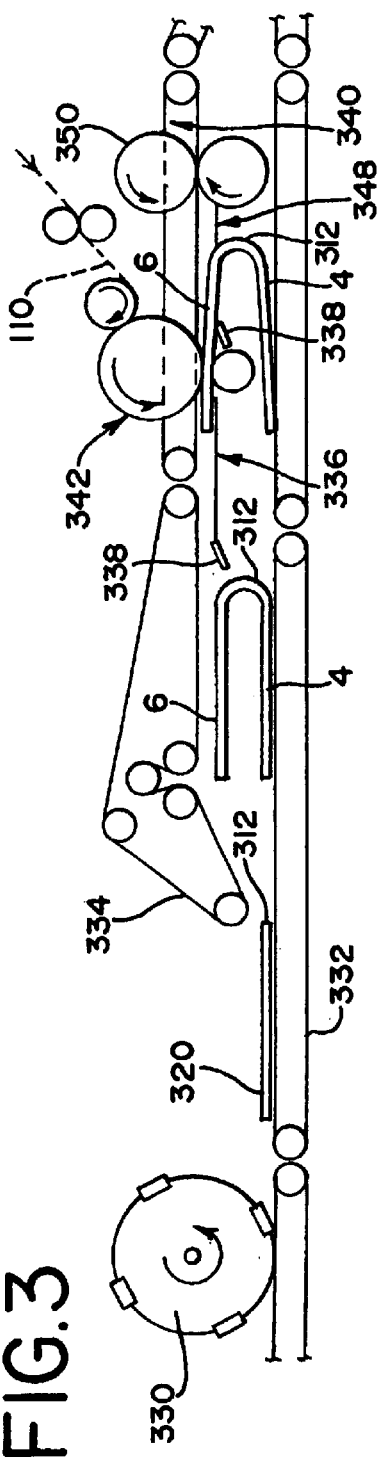
FIG.2
FIG.3

METHOD AND APPARATUS FOR ASSEMBLING REFASTENABLE ABSORBENT GARMENTS

BACKGROUND

The present invention relates generally to a refastenable absorbent garment, and in particular, to a method and apparatus for assembling refastenable absorbent garments.

Absorbent garments can be configured in many different forms. For example, absorbent garments can be configured as a pant-type, pull-on garment, or as a diaper-type product that is drawn up between the legs and fastened about the waist with various fastening systems. Pant-type, pull-on garments are often provided with various elastic elements that can conform to the body of the user and provide a comfortable, snug fit. Often, pant-type garments have a front and rear body panel that are attached along the side edges thereof to form one or more side seams. Such garments, however, often do not have a refastenable mechanism that allows the garment to be easily removed after use or to be adjusted during use.

On the other hand, diaper-type products, which can be configured with fastening systems that allow the user to detach and reattach various fasteners so as to provide a refastenable absorbent garment, often are not configured with various elastic elements, for example around the waist, and may not conform well to the body of the user and/or may provide a bulky appearance beneath the user's garments. Therefore, there remains a need for an improved absorbent garment that is refastenable and provides a snug fit with a non-bulky appearance.

In addition, manufacturing facilities are often configured to fabricate one particular type of product. As such, these facilities may not provide the flexibility to transition between fabricating a pull-on type garment and fabricating a refastenable type garment using a single manufacturing line or asset. Therefore the need also remains for improved methods and assemblies for manufacturing refastenable absorbent garments.

SUMMARY

Briefly stated, in one aspect, the invention is directed to a method for assembling a refastenable absorbent garment. The method comprises moving a continuous absorbent garment subassembly in a machine direction, wherein the continuous absorbent garment subassembly comprises a continuous front body panel web, a continuous rear body panel web and a plurality of discrete crotch portions spaced along the machine direction and extending between the continuous front and rear body panel webs. The crotch portions are folded in a cross direction with one of the continuous front and rear body panel webs facing the other of the continuous front and rear body panel webs. The method further comprises successively cutting the continuous front and rear body panels of the continuous absorbent garment subassembly in the cross direction and thereby forming a plurality of discrete absorbent garment subassemblies, each of which comprises a front body panel and a rear body panel, wherein the front and rear body panels are connected with the crotch portion. Each of the front and rear body panels have opposite side edges, wherein the side edges form the leading and trailing edges of the discrete absorbent garment subassemblies in the machine direction. The method further includes successively rotating each of the discrete absorbent garment subassemblies such that the side edges are spaced apart in the cross direction. The method further comprises attaching a fastener member to at least one of the front and rear body panels on each of the discrete absorbent garment subassemblies.

In one preferred embodiment of the invention, a bodyside surface of each of the front and rear body panels are in contact, and the method further comprises separating the front and rear body panels prior to attaching the fastener member to at least one of the front and rear body panels.

In yet another preferred embodiment, each of the front and rear body panel webs comprise a plurality of elastic elements applied thereto along the machine direction.

In another aspect of the invention, an apparatus for fabricating a refastenable absorbent garment includes a product rotator adapted to rotate the absorbent garment from a cross direction to a machine direction, at least one vacuum conveyor positioned downstream of the product rotator and adapted to separate the front and rear body panels, and a fastener applicator positioned downstream of the at least one vacuum conveyor and adapted to apply a fastener member to at least one of the front and rear body panels.

The present invention provides significant advantages over other absorbent garments and methods and apparatus for the manufacture thereof. For example, by making the absorbent garment refastenable, it can be applied without needing to pull the garment on or off like a pant-like garment. In addition, the garment can be made bigger or smaller simply by adjusting the positioning of the fasteners. Moreover, in one particular application, wherein the garment is used by adults, for example with occasional incontinence problems, the fastening system may be disengaged and engaged repeatedly by the user while the garment remains unsoiled over an extended period of time.

In one preferred embodiment, the absorbent garment includes elastic elements extending along the waist region. The elastic elements provide a snug, comfortable fit that does not create a bulky appearance beneath the user's outer garments. The combination of refastenable fasteners and elastic elements further enhances the fit and appearance of the garment.

At the same time, the manufacturer can easily switch between the manufacture of a non-refastenable, pant-type product and a refastenable product simply by omitting the step of forming one or more side seams and, instead, by introducing the fastener applicator, and a bonder if desired. Conversely, the fastener applicator can be omitted and the side sealer activated. In this way, the machinery and equipment used to fabricate the body panels and crotch portion can be integrated into both processes, thereby maximizing the use of the assets and reducing the costs and space needed for the manufacturing facility.

The present invention, together with further objects and advantages, will be best understood by reference to the following detailed description taken in conjunction with the accompanying drawings.

BRIEF DESCRIPTION OF THE DRAWINGS

FIG. 2 is a schematic top view representation of a method of fabricating the refastenable absorbent garment.

FIG. 3 is a schematic side view representation of an apparatus for and method of fabricating the refastenable absorbent garment.

DETAILED DESCRIPTION OF THE PRESENTLY PREFERRED EMBODIMENTS

Figure 1:
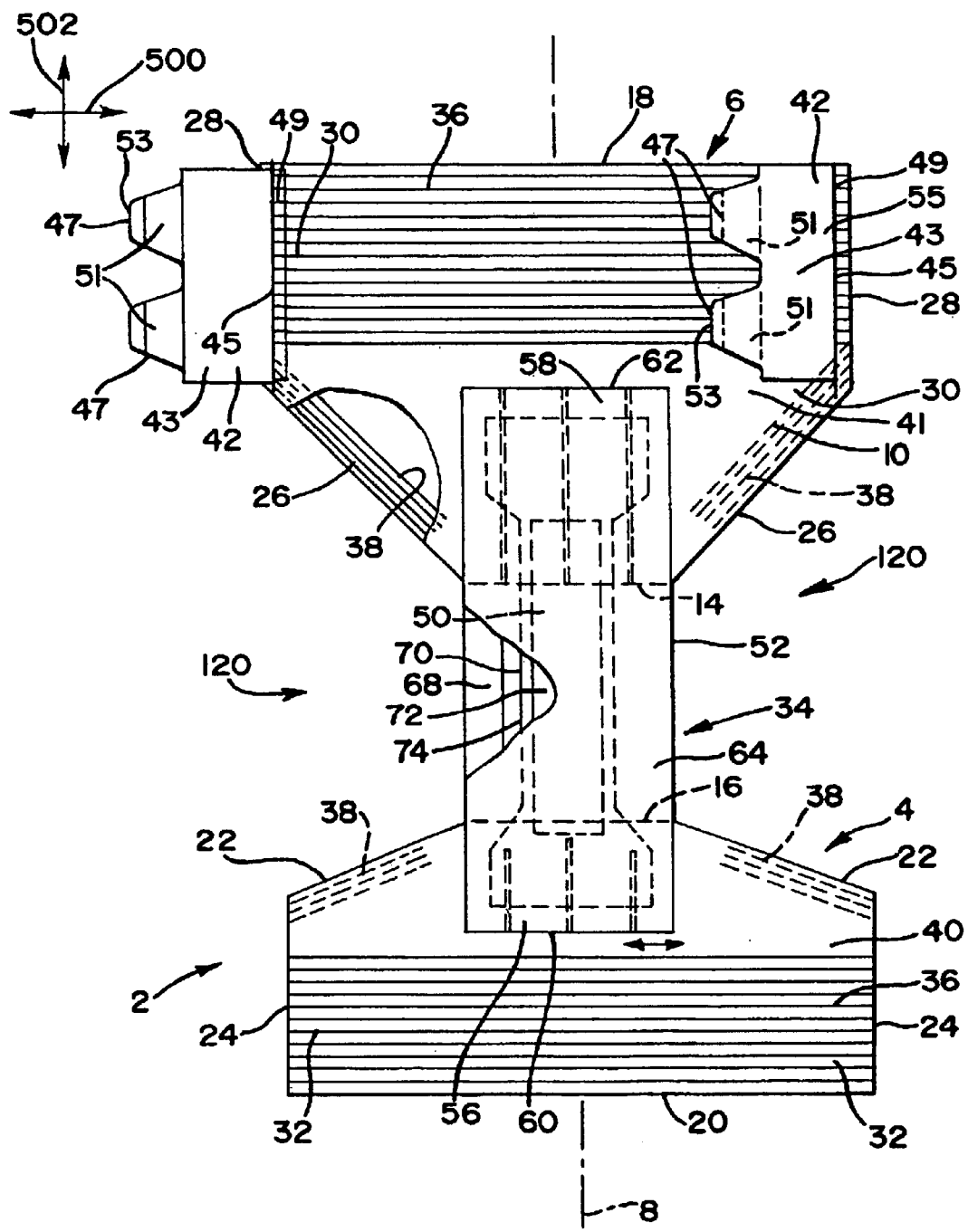
FIG. 1 is a plan top view of one embodiment of a refastenable absorbent garment in an unfastened configuration.

Referring to FIG. 1, it should be understood that the term "longitudinal," as used herein, means of or relating to length or the lengthwise direction 502, and in particular, the direction running between the front and back of the user. The term "laterally," as used herein means situated on, directed toward or running from side to side, and in particular, a direction 500 running from the left to the right of a user, and vice versa. The terms "upper," "lower," "inner," and "outer" as used herein are intended to indicate the direction relative to the user wearing an absorbent garment over the crotch region, while the terms "inboard" and "outboard" refer to the directions relative to a centerline 8 of the garment. For example, the terms "inner" and "upper" refer to a "bodyside," which means the side closest to the body of the user, while the terms "outer" and "lower" refer to a "garment side."

The term "bodyside" should not be interpreted to mean in contact with the body of the user, but rather simply means the side that would face toward the body of the user, regardless of whether the absorbent garment is actually being worn by the user and regardless of whether there are or may be intervening layers between the component and the body of the user. Likewise, the term "garment side" should not be interpreted to mean in contact with the garments of the user, but rather simply means the side that faces away from the body of the user, and therefore toward any outer garments that may be worn by the user, regardless of whether the absorbent garment is actually being worn by a user, regardless of whether any such outer garments are actually worn and regardless of whether there may be intervening layers between the component and any outer garment.

The term "machine direction" means the direction of flow as the various members and webs progress along the fabrication line and process. It should be understood that various separate members or webs can each be traveling in a machine direction, but with the various machine directions not necessarily being parallel or oriented in the same direction. For example, one web may be traveling a first machine direction, which is substantially perpendicular to the travel of another web in a second machine direction.

The term "cross direction" means the direction substantially perpendicular to the machine direction.

The term "downstream" means that one item is positioned more closely to the output or finished product end of the machine and/or process relative to another item. Conversely, the term "upstream" means that an item is positioned more closely to the input end of the machine or process relative to another item. For example, the output end is downstream of the input end, and vice versa, the input end is upstream of the output end.

The phrases "removeably attached," "removeably attaching," "removeably connected," "removeably engaged," "releasably attached," "releasably connected," or "releasably engaged," or variations thereof, refers to two or more elements being connected or connectable such that the elements tend to remain connected absent a separation force applied to one, both or all of the elements, and where the elements are capable of being separated upon the application of a separation force. The required separation force is typically beyond that encountered while wearing the absorbent garment.

The phrases "fixedly secured," "fixedly engaged," "fixedly attached," "fixedly connected," and variations thereof, refers to two or more elements being connected or connectable such that they are not disconnected or otherwise separated, and are not intended to be separated or disconnected, during the normal operation and use of the absorbent garment.

The term "web" refers to a continuous stream of material, whether made from one or more layers or substrates, and regardless of whether it may have noncontinuous, discrete items disposed thereon.

Referring to FIG. 1, an absorbent garment 2 includes a first, front body panel 4 and a second, rear body panel 6. The term "body panel" refers to the portion(s) of the absorbent garment, whether made of one or more layers or substrates or of one or more pieces or components, that is/are fitted circumferentially around at least the waist region of the user, including for example the user's lower back, buttock, hips and abdomen. The first and second body panels each have an inner, bodyside surface 10 and an outer, garment side surface 12. The first, front body panel 4 has a length, which is measured between opposed first and second terminal edges 16 and 20, and which is preferably less than the overall length of the absorbent garment. Likewise, the second, rear body panel 6 has an overall length, which is measured between opposed first and second terminal edges 14 and 18, and which is also preferably less than the overall length of the absorbent garment. Each of the first and second body panels has an outboard edge 24, 28 formed along the outer periphery of laterally opposed side portions of the first and second body panel. It should be understood that the outboard edges of the front and rear body panels can be different lengths.

In one embodiment, each of the first and second body panels includes a tapered edge 22, 26 and laterally opposed side, ear portions 30, 32, the outer periphery of which forms the outboard edges 24, 28. Alternatively, the terminal edges of the body panels can run laterally along the entire width of thereof without any tapered portions. In one preferred embodiment, the first terminal edges 14, 16 of the first and second body panels are longitudinally spaced to form an opening 34 therebetween in the crotch region of the garment, while the second terminal edges 20, 18 of the first and second body panels form front and back waist edges respectively.

Referring to FIG. 1, one or more, and preferably a plurality, meaning two or more, laterally extending elastic elements 36 are secured to each of the first and second body panels. Preferably, a plurality of laterally extending elastic elements are longitudinally spaced across substantially the entire length of the waist portion of the rear body panel 6, although they may be spaced across a lesser length. In one embodiment, the front body panel has a "non-elasticized" area wherein there are no laterally extending elastic elements, or other elastic or elastomeric backing members, incorporated therein or making up any portion of the thickness or cross-section of the body panel at that area, such that the material can be gathered. It should be understood, that in other alternative embodiments, one or more separate waist bands, with or without elastic elements, can be secured to one or both of the rear and front body panels, preferably along the upper terminal edges thereof. In addition, one or both of the body panels can be formed without any elastic elements.

In yet another alternative embodiment, the front body panel has a "deactivated" area wherein the elastic elements are severed, chopped or otherwise deactivated, for example by using a rotary die cutter, by melt-breaking (e.g. with a heated or ultrasonic function roll or by any other means known to those skilled in the art. In one preferred embodiment, the deactivated area or landing zone is formed along a center portion of the front body panel and underlies a landing member or patch, which is secured thereover on the garment side of the front body panel. The laterally extending elastic elements can be spaced longitudinally across the entire length of the front body panel, or along a lesser length. For example, the elastic elements can extend laterally along the upper waist portion and along the lower terminal edge defining the leg opening. One or more leg elastic elements 38 can be secured along the inner terminal edges of the body panels 4, 6 and an absorbent composite 50 to form a gasket with the leg of the user.

The various waist and leg elastic elements can be formed from rubber or other elastomeric materials. One suitable material is a LYCRA® elastic material. For example, the various elastic elements can be formed of LYCRA® XA Spandex 540, 740 or 940 detex T-127 or T-128 elastics available from E. I. duPont De Nemours and Company, having an office in Wilmington, Del.

Each body panel is preferably formed as a composite, or laminate material, otherwise referred to as substrates or laminates, with the plurality of elastic strands sandwiched therebetween. Preferably two, or more, layers are bonded with various adhesives, such as hot melt, or by other techniques, including for example and without limitation ultrasonic bonding and heat pressure sealing. In one embodiment, the two layers are made of a non-woven material. It should be understood that the body panels can be made of a single layer or substrate of nonwoven material, or can be comprised of more than two layers or substrates. Of course, it should be understood that other knitted or woven fabrics, non-woven fabrics, elastomeric materials, polymer films, laminates and the like can be used to form one or more of the body panel layers. The term "non-woven" web or material, as used herein, means a web having a structure of individual fibers or filaments that are interlaid, but not in an identifiable manner and without the aid of textile weaving or knitting, as in a knitted or woven fabric.

In one embodiment, the non-woven layers or substrates, and also a landing material, can be made by spunbonding. Spunbond nonwoven webs or materials are made from melt-spun filaments or spunbonded fibers which refers to small diameter fibers that are formed by extruding molten thermoplastic material as filaments from a plurality of fine, usually circular capillaries of a spinneret with the diameter of the extruded filaments then being rapidly reduced, for example, by non-eductive or eductive fluid-drawing or other well known spunbonding mechanisms. The production of spunbound nonwoven webs is described in U.S. Pat. No. 4,340,563 to Appel et al., U.S. Pat. No. 3,692,618 to Dorschner et al., U.S. Pat. No. 3,802,817 to Matsuki et al, U.S. Pat. No. 3,502,763 to Hartmann, U.S. Pat. No. 3,276,944 to Levy, U.S. Pat. No. 3,502,538 to Peterson, and U.S. Pat. No. 3,542,615 to Dodo et al, all of which are incorporated herein by reference. The melt-spun filaments formed by the spunbond process are generally continuous and have diameters larger than 7 microns, more particularly, between about 10 and 30 microns. Another frequently used expression of fiber or filament diameter is denier, which is defined as grams per 9000 meters of a fiber or filament. The fibers may also have shapes such as those described in U.S. Pat. No. 5,277,976 to Hogle, et al, U.S. Pat. No. 5,466,410 to Hills and U.S. Pat. Nos. 5,069,970 and 5,057,368 to Largman et al., all of which are incorporated herein by reference. The spunbond filaments usually are deposited, by one or more banks, onto a moving foraminous belt or forming wire where they form a web. Spunbonded filaments generally are not tacky when they are deposited onto the collecting surface.

Spunbond fabrics typically are stabilized or consolidated (pre-bonded) in some manner immediately as they are produced in order to give the web sufficient integrity to withstand the rigors of further processing into a finished product. This stabilization (prebonding) step may be accomplished through the use of an adhesive applied to the filaments as a liquid or powder which may be heat activated, or more commonly, by compaction rolls. As used herein, the term "compaction rolls" means a set of rollers above and below the web used to compact the web as a way of treating a just produced, melt-spun filament, particularly spunbond, web, in order to give the web sufficient integrity for further processing, but not the relatively strong bonding of secondary bonding processes, such as through-air bonding, thermal bonding, ultrasonic bonding and the like. Compaction rolls slightly squeeze the web in order to increase its self-adherence and thereby its integrity.

An alternative means for performing the pre-bonding step employs a hot air knife, as described in U.S. Pat. No. 5,707,468, which is hereby incorporated herein by reference in its entirety. Briefly, the term "hot air knife" means a process of pre-bonding a just produced melt-spun filament, particularly spunbond, web, in order to impart the web with sufficient integrity, i.e., increase the stiffness of the web, for further processing. A hot air knife is a device that focuses a stream of heated air at a very high flow rate, generally from about 300 to about 3000 meters per minute (m/min.), or more particularly from about 900 to about 1500 m/min., directed at the nonwoven web immediately after its formation. The air temperature usually is in the range of the melting point of at least one of the polymers used in the web, generally between about 90° C. and about 290° C. for the thermoplastic polymers commonly used in spunbonding. The control of air temperature, velocity, pressure, volume and other factors helps avoid damage to the web while increasing its integrity.

The hot air knife's focused stream of air is arranged and directed by at least one slot of about 3 to about 25 millimeters (mm) in width, particularly about 9.4 mm, serving as the exit for the heated air towards the web, with the slot running in a substantially cross-machine direction over substantially the entire width of the web. In other embodiments, there may be a plurality of slots arranged next to each other or separated by a slight gap. The at least one slot usually, but not necessarily, is continuous, and may be comprised of, for example, closely spaced holes. The hot air knife has a plenum to distribute and contain the heated air prior to its exiting the slot. The plenum pressure of the hot air knife usually is between about 2 to about 22 mmHg, and the hot air knife is positioned between about 6.35 mm and about 254 mm, and more particularly from about 19.05 to about 76.20 mm above the forming surface. In a particular embodiment, the hot air knife plenum's cross-sectional area for cross-directional flow (i.e., the plenum cross-sectional area in the machine direction) is at least twice the total slot exit area. Since the foraminous wire onto which spunbond polymer is formed generally moves at a high rate of speed, the time of exposure of any particular part of the web to the air discharge from the hot air knife typically is less than a tenth of a second and generally about one hundredth of a second, in contrast with the through-air bonding process, which has a much longer dwell time. The hot air knife process has a great range of variability and control over many factors, including air temperature, velocity, pressure, and volume, slot or hole arrangement, density and size, and the distance separating the hot air knife plenum and the web.

The spunbond process also can be used to form bicomponent spunbond nonwoven webs as, for example, from side-by-side (or sheath/core) linear low density polyethylene/polypropylene spunbond bicomponent filaments. A suitable process for forming such bicomponent spunbond nonwoven webs is described in U.S. Pat. No. 5,418,045 to Pike et al., which is incorporated herein by reference in its entirety.

Commercially available thermoplastic polymeric materials can be advantageously employed in making the fibers or filaments from which pattern-unbonded nonwoven material is formed. As used herein, the term "polymer" shall include, but is not limited to, homopolymers, copolymers, such as, for example, block, graft, random and alternating copolymers, terpolymers, etc., and blends and modifications thereof. Moreover, unless otherwise specially limited, the term "polymer" shall include all possible geometrical configurations of the material, including, without limitation, isotactic, syndiotactic and random symmetries. As used herein, the terms "thermoplastic polymer" or "thermoplastic polymeric material" refer to a long-chain polymer that softens when exposed to heat and returns to its original state when cooled to ambient temperature. Preferably, the spunbond fibers are made of a polypropylene. Other alternative thermoplastic materials include, without limitation, poly (vinyl chloride)s, polyesters, polyamides, polyfluorocarbons, polyolefins, polyurethanes, polystyrenes, polyethylenes, poly(vinyl alcohol)s, caprolactams, and copolymers of the foregoing. The fibers or filaments used in making the nonwoven material may have any suitable morphology and may include hollow or solid, straight or crimped, single component, bicomponent or multicomponent, biconstituent or multiconstituent fibers or filaments, and blends or mixes of such fibers and/or filaments, as are well known in the art.

After the nonwoven web is formed, the pre-bonded or unbonded web is passed through a suitable process or apparatus, including for example a calendar roll, to form a pattern of discrete bonded areas. The term "discrete" as used herein means individual or disconnected, and is contrasted with the term "continuous" as used in U.S. Pat. No. 5,858,515 to Stokes et al, the entirety of which is hereby incorporated by reference and which describes pattern-unbonded, or point unbonded, nonwoven fabrics having continuous bonded areas defining a plurality of discrete unbonded areas. In one embodiment, the calendar stack (not shown) includes an anvil roll and a pattern roll, which is heated and includes various raised landing portions. The raised portions of the pattern roll thermally bond the fibers to form the bonded areas. The bonds can made of any shape and size. Preferably, the percent bonded area of the web is between about 5% and 25% of the area of the web, and is more preferably between about 10% and 15%. Thereafter, the bonded substrate can be bonded to another substrate with the elastic members disposed therebetween.

In one alternative preferred embodiment, the landing material is made of a point-unbonded nonwoven material, for example, a 2.0 osy point-unbonded material. One exemplary material of this type has been used in a HUGGIES® Ultratrim Disposable Diaper, which is commercially available from Kimberly-Clark Corporation. In another preferred embodiment, the landing material is made of a non-woven spunbond material, for example, a spunbond material having a basis weight of preferably about 0.6 osy. In other preferred embodiments, the basis weight of each substrate can be between at least about 0.3 and about 2.0 osy, and preferably between about 0.5 osy and about 1.5 osy, and more preferably between about 0.5 osy and about 1.0 osy. Even with a relatively low percent area bonding, the relatively low basis weight non-woven spunbond material exhibits strength and tear characteristics allowing it to be used as a body panel. Other materials that may be used as the non-woven material include various meltblown materials, and also bonded-carded materials.

In other alternative embodiments, the landing material can be made of a loop material, which typically includes a backing structure and a plurality of loop members extending upwardly therefrom. The loop material can be formed from any suitable material, such as acrylic, nylon or polyester, and can be formed from such methods as warp knitting, stitch bonding or needle punching. Suitable loop materials are available from Guilford Mills, Inc., Greensboro, N.C., U.S.A. under the trade designation No. 36549.

The body panel 4, 6 non-woven material is preferably substantially hydrophobic, which may optionally be treated with a surfactant or otherwise process to impart a desired level of wettability and hydrophilicity. In one particular embodiment of the invention, the body panel is a nonwoven, wireweave spunbond polypropylene fabric composed of about 1.6 denier fibers formed into a web having a basis weight of about 0.6 osy. One suitable non-woven material is the Corinth 0.60 osy, 1.6 dpf wireweave, nonwettable Metallocene (EXXON ACHIEVE 2854 PP) spunbond material manufactured by Kimberly-Clark Corporation, the assignee of the present application.

Refering to FIG. 1, fastening members or tabs 42 are attached to and extend laterally inboard from the outboard side edge 28 of the rear body panel 6 from an attachment location 45. In one embodiment, the front body panel 4 includes a middle portion having a landing member secured thereto. The landing member is configured to mate with or be engaged by the fastening members. For example, the landing member can be made of a loop material that engages hooks forming part of the fastener member. In other embodiments, the fastener member simply engages the front body panel substrate material, in either a non-elasticized area, or an elasticized area that includes elastic elements, for example. Preferably, the fastening members 42 are fixedly secured to the garment-side surface of the side portions 30 of the rear body panel along the side edges 28 thereof. In another preferred embodiment, the fastener members 42 are fixedly secured to the body side surface 10 of the side portions of the rear body panel, as shown for example in FIG. 1.

It should be understood that, in other embodiments, the fastening members can be secured to one or both of the front body panel and rear body panel and releasably or removeably engage either of the front and rear body panels. Preferably, the fastening members are fixedly secured to the outer, garment-side surface of the front and/or rear body panels (or the outer cover portion thereof), and releasably engage the outer, garment-side surface of the other of the front and/or rear body panels. However, it should be understood that the fastening members could be fixedly secured to an inner body-side surface of the front and/or rear body panels and releasably engage an inner, body-side surface or outer garment side surface of the front and/or rear body panels.

For the purposes of illustration, the right side fastener member 42 is shown as being folded in over and releasably engaged with the body panel during manufacture, while the left side fastener 42 is shown as being extended outboard, which is the position thereof when it is initially secured to the body panel and also during use. The fastener members can be made of a hook and loop combination, such as a VELCRO® fastening system, or can have adhesive or other bonding agents applied to one surface thereof. As shown in FIG. 1, the fastener member 42 can include one or more attachment pads or refastenable portions 51. Alternatively, the fastener members can include adhesive tape, buttons, snaps, ties or other known fastening devices. The fastener members can be secured to the body panel with adhesive bonds, sonic bonds, thermal bonds, pinning, stitching or other known types of attachment.

Figure 4:
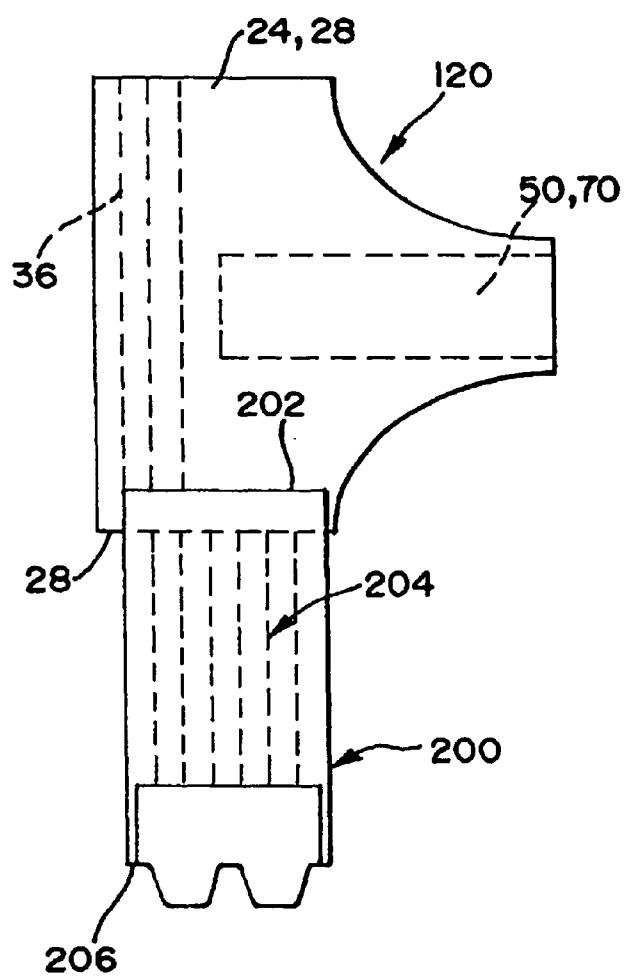
FIG. 4 is a plan top view of an alternative embodiment of a refastenable absorbent garment.

In one alternative embodiment, shown in FIG. 4, the absorbent garment further includes an extension panel 200, which has a first, inboard edge 202 secured to the rear body panel. The extension panel 200 can include laterally extending elastic elements 204, or can be inelastic. The fastener member 42 is secured to an outboard edge 206 of the extension panel. The width of the extension panel, which can be considered to be a carrier member, or as forming part of the fastener member, can be varied so as to provide various size garments suitable for different size users. However, the chassis of the garment can be made a single uniform size, such that the pitch of the machine does not have to be altered. Rather, the size of the garment is adjusted simply by varying the width of the fastener member, or extension panel.

When the absorbent garment is secured to the user, the fastening members 42 secured to the body panels 6 on one end of the absorbent composite releasably or removeably engage or are otherwise connected to the body panels 4 on the opposite end of the garment. When secured in this way, leg openings 120 are formed on each side of the absorbent composite with the peripheral edge 52 of the absorbent composite and outer cover further defining the opening along the crotch region of the garment.

It should be understood that the outboard edges 24, 28 of the front and rear body panels could be connected, for example by bonding or sewing, to create a seam of a pant garment.

It also should be understood that the front and rear body panels can be made as an integral unitary member that extends along the crotch from the front to back and with the sides thereof that can be connected to form leg holes. In such an embodiment, the portion of the unitary member fitted around the front of the user is defined as the front body panel, with the portion fitted around the rear of the user being the rear body panel. Alternatively, the front and rear body panels can be formed integrally as a ring, for example as one panel extending around the waist and hips of the user, with portions of the ring forming the front and rear body panels.

In one preferred embodiment, an outer cover is disposed over the entire garment and forms the outer garment side layer or substrate of the front and rear body panels, with the various elastic elements 38, 36 disposed between an bodyside liner layer of the front and rear body panels, which liners are preferably configured as a single substrate, and the outer cover, which also is preferably configured as a single substrate. In this way, the portion of the outer cover that overlies the front body panel liner and is fitted around the front of the user forms part of the front body panel, while the portion of the outer cover that overlies the rear body panel liner and is fitted around the rear of the user forms part of the rear body panel. The front and rear body panels, with the outer cover forming portions thereof and preferably extending therebetween, forms a chassis. The outer cover is preferably made of a non-woven material, similar to that of the other body panel materials described herein. It should be understood that the body panels, including the outer cover, can be configured with any number of a plurality of substrates, and that the body panels can include other layers or substrates.

Preferably, as shown in FIG. 1, the fastening members 42 comprise a carrier member 43 that is formed in a generally side-ways, "U" shape, with a vertical extending base member 55 and a pair of laterally extending and longitudinally spaced tab members 47. The carrier member could also comprise one or more than two tab members. The carrier members are preferably fixedly secured to the side portions of the rear body panel 6 with one or more adhesive bonds 49, sonic bonds, thermal bonds, pinning, stitching and/or other known types of attachment, as shown for example in FIG. 1. In alternative embodiments, the fastening members can be fixedly secured to the front body panel or to one or both of the front and rear body panels, e.g., at the seam, as explained above.

Each carrier member 43 has a longitudinal length and each of the tab members 47 comprises an refastenable portion or an engagement portion having a longitudinal length. The refastenable portion 51 preferably comprises an array of hooks, as explained below, but alternatively can comprise various adhesives, such as pressure sensitive adhesives, buttons, zippers, snaps and other releasable and reattachable fastening devices known to those skilled in the art.

In one embodiment, shown in FIGS. 1 and 2, each fastening member 42 is comprised of two separate, longitudinally spaced tab members 47. In any of the embodiments, the two or more tab members provides a pant-like fit that controls the waist and leg openings in the front and back of the garment, and also allows the user to adjust the fit of the garment without totally undoing the garment. For example, the user can release one of the tab members 47 on one of the fastening members 42 and refasten it without undoing the other tab member on that same fastening member. It should be understood that the fastener member can be configured with a single tab, or can have a rectangular shape with one or more refastenable patches secured thereto.

In one preferred embodiment, the refastenable portion 51 comprises a hook-type fastener member, or hook strip, which is secured to the carrier member 43 with adhesive, ultrasonic bonding, stitching or other known attachment devices. The end portion 53 or tip of the carrier member can be left uncovered by the refastenable portion 51, such that it can be lifted or flexed and grasped by a user as they disengage or peel back the fastener member. It should be understood that the term "hook" as used herein means any element capable of engaging another element, and is not intended to limit the form of the engaging elements, for example to include only "hooks," but rather encompasses any form or shape of engaging element, whether unidirectional or bidirectional. Various hook configurations are described in U.S. Pat. No. 5,845,375 to Miller et al., U.S. Pat. No. 6,132,660 to Kampfer, U.S. Pat. No. 6,000,106 to Kampfer, U.S. Pat. No. 5,868,987 to Kampfer, U.S. Pat. No. 4,894,060 to Nestegard, and U.S. Pat. No. 6,190,594 B1 to Gorman, the entire disclosures of which are incorporated by reference herein. Some examples of hook fasteners are the various CS600 hook fasteners, including the XKH-01-002 CS600, 2300 Pin Density hook fastener (Part No. XKH-01-002/60MM/SP#2628), manufactured by Minnesota Mining and Manufacturing Co., St. Paul Minn. Another example of a hook fastener is the Velcro® HTH-851 and HTH-829 hook fasteners available from Velcro USA, Inc.

In one preferred embodiment, a mushroom-type hook strip comprises a homogeneous backing of thermoplastic resin and, integral with backing, an array of upstanding stems distributed across at least one face of the backing, each having a mushroom head. The array of hooks on each strip comprise an engagement portion having a longitudinal length. The stems can have a molecular orientation as evidenced by a birefringence value of at least 0.001, and the mushroom heads having circular disc shapes with generally planar end surfaces opposite the backing, which disc shaped heads preferably have diameter to thickness ratios of greater than about 1.5 to 1.

The stems of the hook strip can be molecularly orientated as evidenced by a birefringence value of at least 0.001. As such, they have significantly greater stiffness and durability, as well as greater tensile and flexural strength, than would be achievable without such orientation. Because of these qualities, the portions of the stems not heated by a heating surface during the forming process remain resiliently flexible during a deforming step, which preferably involves the application of heat to the stem tips by contact with the heated surface of a metal roller. Such contact forms the tip of each stem into a circular disc shaped mushroom head at the tip of each stem, which head has a substantially flat inner surface that enhances its holding power when engaged with a loop.

As compared to hook strips that have unoriented stems, the enhanced strength of the hooks of the hook strip makes them less likely to break during disengagement. When the hook strip is used with the non-woven material herein described, the enhanced strength of the hooks makes them less likely to break under disengagement forces than the fibers of the material, a beneficial attribute for at least two reasons. First, broken hooks can create debris whereas a broken fiber typically does not. Furthermore, the non-woven material typically contains many more engageable fibers than there are hooks per unit area, thus allowing a greater number of disengagements before a hook-and-loop fastener becomes useless.

Although the stems of the hook strip preferably are generally circular in cross section, other suitable cross sections include rectangular and hexagonal. The stems preferably have fillets at their bases, both to enhance strength and stiffness and for easy release from a mold in which they are formed. In addition, the stems can be tapered, preferably from a larger to a smaller cross-section as one moves from the base to the head.

The stem portions are preferably at an angle of about 90 degrees from the backing substrate, however, this angle can range from about 80 to about 100 degrees, preferably 85 to about 95 degrees. The hook head portion is formed on the distal end of the stem. The hook head can be elongated in on or more directions forming the fiber engaging portions. These fiber engaging portions extend outward from the stem portion at any angle so that they can project upwardly away from the film backing, parallel with the film backing or even downward toward the film backing.

For example, the hook head portion has a deformed fiber engaging portion that projects downward. Preferably, the lower surface of the fiber engaging portion also projects downward form a crook between the lower face of the fiber engaging portion and the stem base portion. In one preferred embodiment, the heads of the hooks generally project at a downward angle from the hook head top portions toward the base. This downward angle (measured from a reference line taken from the top of the hook head and parallel with the backing) is generally from about 0 to about 70 degrees, preferably from about 5 to about 60 degrees and most preferably from about 5 to about 35 degrees (defined by a linear extent running from a center region of the hook head top portion to an end of the hook head fiber engaging portion).

The head shape with its high diameter to thickness ratio, and the small size and close spacing or high density of individual hooks that are provided by the hook strip according to the present invention makes it able to easily firmly releasably engage non-woven materials in shear, possibly because the many thin heads can easily move radially into engagement with rather small fibers. Thus the hook strip is particularly useful for hook-and-loop fastening when the "loops" are provided by non-woven materials which are not particularly adapted for use as the loop portions of hook and loop fasteners, and which are not as well engaged by known prior art hook strips. For example, the hook strip is particularly well-suited for engaging the topographically flatter non-woven materials described above, including the non-woven spunbond material, which has relatively fewer loose, outwardly extending, free fibers than conventional loop materials, but still provides a relatively high number of pores, of sufficient size, such that the material can be engaged by the hooks. Indeed, once the hooks are received in the pores, or embedded in the non-woven material, the fastening tabs provide excellent shear characteristics, such that the garment is securely fastened during normal wearing conditions.

In general, the hooks are of uniform height, preferably of from about 0.10 to 1.30 mm in height, and more preferably from about 0.18 to 0.51 mm in height; have a density on the backing preferably of from 60 to 1,600 hooks per square centimeter, and more preferably from 125 to 690 hooks per square centimeter, and preferably greater than about 150 hooks per square centimeter; have a stem diameter adjacent the heads of the hooks preferably of from 0.07 to 0.7 mm, and more preferably from about 0.1 to 0.3 mm. The deformed hook heads project radially past the stems on at least one side preferably by an average of about 0.01 to 0.3 mm, and more preferably by an average of about 0.02 to 0.25 mm and have average thicknesses between their outer and inner surfaces (i.e., measured in a direction parallel to the axis of the stems) preferably of from about 0.01 to 0.3 mm and more preferably of from about 0.02 mm to 0.1 mm. The hook heads have average head diameter (i.e., measured radially of the axis of the heads and stems) to average head thickness ratio preferably of from 1.5:1 to 12:1, and more preferably from 2.5:1 to 6:1.

For most hook-and-loop uses, the hooks of the hook strip should be distributed substantially uniformly over the entire area of the hook strip, usually in a square or hexagonal array.

To have both good flexibility and strength, the backing of the hook strip preferably is from 0.02 to 0.5 mm thick, and more preferably is from 0.06 to 0.3 mm in thick, especially when the hook strip is made of polypropylene or a copolymer of polypropylene and polyethylene. For some uses, a stiffer backing could be used, or the backing can be coated with a layer of pressure sensitive adhesive on its surfaces opposite the hooks by which the backing could be adhered to a substrate, such as the carrier member 43, so that the backing could then rely on the strength of the substrate to help anchor the hooks.

Virtually any orientable thermoplastic resin that is suitable for extrusion molding may be used to produce the hook strip. Thermoplastic resins that can be extrusion molded and should be useful include polyesters such as poly(ethylene terephthalate), polyamides such as nylon, poly(styrene-acrylonitrile), poly(acrylonitrile-butadiene-styrene), polyolefins such as polypropylene, and plasticized polyvinyl chloride. One preferred thermoplastic resin is a random copolymer of polypropylene and polyethylene containing 17.5% polyethylene and having a melt flow index of 30, that is available as SRD7-463 from Shell Oil Company, Houston, Tex.

The hook strip has preferably substantially continuous planar backing of thermoplastic resin. Integral with the backing is the array of hooks projecting generally at right angles to one major surface of the backing. Each of the hooks has a stem, and, at the end of the stem opposite the backing, a generally circular plate-like cap or head projecting radially past or overhanging the stem so as to form a fiber engaging portion that projects downward. Preferably, the lower surface of the fiber engaging portion also projects downward form a crook between the lower face of the fiber engaging portion and the stem base portion. The stem can also have a fillet around its base.

When the absorbent garment is secured to the user, the fastening tabs 42 secured to the side portions of the rear body panels 6 releasably engage or are otherwise connected to the front body panel 4, which may include the landing member. In particular, the heads on the hooks engage the fibers of the body panel, whether elasticized or not, or the landing material making up the landing member.

Referring to FIGS. 1 and 2, the absorbent garment includes an absorbent composite 50 having first and second longitudinally opposed terminal end edges 60, 62. The absorbent composite preferably includes a substantially liquid permeable topsheet 64, or liner, and a substantially liquid impermeable backsheet 68, or outer cover. A retention portion 70 is disposed or sandwiched between the topsheet and the backsheet, which are connected. The topsheet, backsheet and other components of the absorbent composite 50 can be joined for example with adhesive bonds, sonic bonds, thermal bonds, pinning, stitching or any other attachment techniques known in the art, as well as combinations thereof. For example, a uniform continuous layer of adhesive, a patterned layer of adhesive, a sprayed pattern of adhesive or any array of lines, swirls or spots of construction bonds may be used to join the topsheet and backsheet, or any of the other components described herein. It should be understood that the term "absorbent composite" refers to any material or assembly capable of absorbing liquids or bodily exudates, and may be comprised of a single material or component, for example a retention portion.

Additional layers, including for example, a surge layer 72, are also preferably incorporated into the absorbent composite. Preferably, the surge layer does not run the entire length of the absorbent composite and is shorter than the retention portion. The topsheet can be indirectly joined to the backsheet by affixing the topsheet to intermediate layers, such as the surge layer or retention portion, which in turn is affixed to the backsheet. The absorbent composite may also include barrier cuffs, or leakage control shields, formed along the opposite longitudinally extending edges of the absorbent composite.

The backsheet 68 is preferably liquid impermeable, but may be liquid permeable, e.g., when an additional barrier layer is used with the retention portion. For example, in one embodiment, the backsheet can be made from a thin plastic film, or other flexible, substantially liquid-impermeable material. As used herein, the term "flexible" means a material that is compliant and which will readily conform to the general shape and contour of the body of the user. The backsheet prevents various bodily fluids and exudates from wetting or otherwise contaminating various bedding or outer garments worn by the user over the absorbent garment. In particular, the backsheet can include a film, such as a polyethylene film, having a thickness of from about 0.012 mm to about 0.051 mm.

In various constructions, the topsheet can comprise various woven or nonwoven materials. For example, the topsheet can be composed of a meltblown or spunbonded web of desired fibers, and may also be a bonded-carded web. For example, the topsheet can be made of a substantially hydrophobic material, and the hydrophobic material may optionally be treated with a surfactant or otherwise processed to import a desired level of wettability and hydrophilicity. In one particular embodiment of the invention, the topsheet is a nonwoven, spunbond polypropylene fabric composed of about 2.8–3.2 denier fibers formed into a web having a basis weight of about 22 gsm and density of about 0.06 gm/cc. The fabric can be surface treated with an operative amount of surfactant, such as about 0.28% Triton X-102 surfactant. The surfactant can be applied by any conventional means, such as spraying, printing, brush coating or the like.

In various constructions, the backsheet can comprise a woven or nonwoven fibrous web layer, which is treated or constructed, partially or wholly, to impart the desired levels of liquid impermeability to selected regions that are adjacent to or proximate the absorbent retention portion. For example, the backsheet may include a gas-permeable, nonwoven fabric layer laminated to a polymer film layer which may or may not be gas-permeable. Other examples of fibrous, cloth-like backsheet materials can comprise a stretch thinned or stretch thermal laminate material composed of a 0.6 mil (0.015 mm) thick polypropylene cast film and a 0.7 ounce per square yard (23.8 gsm) polypropylene spunbond material (2 denier fibers). A material of this type has been employed to form the outercover of a HUGGIES® Ultratrim Disposable Diaper, which has been commercially available from Kimberly-Clark Corporation. The backsheet can provide the outercover of the article, particularly in the crotch region. Optionally, however, the article may include a separate outercover component member, as explained above, which is additional to the backsheet. The outercover can be joined, for example, to one or more of the absorbent composite and/or body panels as explained above.

The backsheet may include a micro-porous, "breathable" material which permits gases, such as water vapor, to escape from the absorbent garment while substantially preventing liquid exudates from passing through the backsheet. For example, the breathable backsheet may be composed of a microporous polymer film or a nonwoven fabric which has been coated or otherwise modified to impart a desired level of liquid impermeability. For example, a suitable microporous film can be a PMP-1 material, which is available from Mitsui Toatsu Chemicals, Inc., a company having offices in Tokyo, Japan; or an XKO-8044 polyolefin film available from 3M Company of Minneapolis, Minn. The backsheet may also be embossed or otherwise provided with a pattern or matte finish to exhibit a more aesthetically pleasing appearance.

In various configurations of the invention, where a component, such as the backsheet is configured to be permeable to gas while having a resistance and limited permeability to aqueous liquid, the liquid resistant component can have a construction which is capable of supporting a selected hydrohead of water substantially without leakage therethrough. A suitable technique for determining the resistance of a material to liquid penetration is Federal Test Method Standard FTMS 191 Method 5514, 1978, or an equivalent thereof.

In one preferred embodiment, the backsheet is sufficiently impermeable to liquid and semi-liquid materials to substantially prevent the undesired leakage of waste materials, defined as exudates, including for example urine and feces. For example, the backsheet member can desirably support a hydrohead of at least about 45 centimeters (cm) substantially without leakage. The backsheet member can alternatively support a hydrohead of at least about 55 cm, and optionally, can support a hydrohead of at least about 60 cm, or more, to provide improved benefits.

The outer cover and/or backsheet also can be extensible. In one preferred embodiment, the backsheet and/or outer cover is capable of providing an elongation of at least about 1 cm when subjected to a tensile force of 11.8 g/cm, and further provides a substantially permanent deformation of at least about 20% when subjected to a tensile force of 19.70 g/cm and is then allowed to relax under a zero applied stress for a period of 1 minute.

For example, the extensible member can be composed of a necked fiber, a creped fiber, a micro-pleated fiber, polymer films or the like, as well as combinations thereof. The fabrics may be woven or nonwoven materials, such as spunbond fabrics. One example of a suitable extensible material is a 60% necked, polypropylene spunbond having a basis weight of about 1.2 osy.

The backsheet and/or outer cover also can be expandable, for example when it has one or more folds, e.g., one or more z-folds (not shown), or can be both extensible and expandable. The term expandable as used herein means to enlarge or to increase the extent or area, lateral and/or longitudinal, thereof, e.g., by unfolding one or more folds.

The retention portion 70 is preferably made of an absorbent material, which can be any material that tends to swell or expand as it absorbs exudates, including various liquids and/or fluids excreted or exuded by the user. For example, the absorbent material can be made of airformed, airlaid and/or wetlaid composites of fibers and high absorbency materials, referred to as superabsorbents. Superabsorbents typically are made of polyacrylic acids, such as FAVOR 880 available from Stockhausen, Inc. of Greensboro, N.C. The fibers can be fluff pulp materials, such as Alliance CR-1654, or any combination of crosslinked pulps, hardwood, softwood, and synthetic fibers. Airlaid and wetlaid structures typically include binding agents, which are used to stabilize the structure. In addition, various foams, absorbent films, and superabsorbent fabrics can be used as an absorbent material. Various acceptable absorbent materials are disclosed in U.S. Pat. Nos. 5,147,343 for Absorbent Products Containing Hydrogels With Ability To Swell Against Pressure, 5,601,542 for Absorbent Composite, and 5,651,862 for Wet Formed Absorbent Composite, all of which are hereby incorporated herein by reference. Furthermore, the proportion of high-absorbency particles can range from about 0 to about 100%, and the proportion of fibrous material from about 0 to about 100%. Additionally, high absorbency fibers can be used such as Oasis type 121 and type 122 superabsorbent fibers available from Technical Absorbent Ltd., Grimsby, Lincolnshire, United Kingdom.

The retention portion 70 has laterally opposed side edges 74 and preferably can be made of a single or dual layer of absorbent material. The retention portion preferably has an hour-glass shape with enlarged end regions. Alternatively, the retention portion can include a folded or multi-layered configuration. The retention portion preferably has a length substantially equal to, or slightly shorter than, the length of the absorbent composite. The retention portion can include one or more barrier layers attached to the absorbent material. In one embodiment, an upper tissue substrate is disposed adjacent the retention portion. Alternatively, a lower tissue substrate can be disposed adjacent an opposite side of the retention portion, or the tissue can completely envelope the retention position.

Referring to FIG. 1, the opposite garment side of the end regions of the absorbent composite, and in particular, the outer, garment side surface of the backsheet 68, are secured to the bodyside surface of the longitudinally opposed crotch ends of the first and second body panels 4, 6. Alternatively, it should be understood that the body side surface of the absorbent composite can be attached to the garment side of the body panels. In one preferred embodiment, the outer cover also makes up part of the body panels, and has a bodyside surface thereof attached to the absorbent composite along the crotch region between the ends of the front and rear body panels. It should be understood that the absorbent composite can be secured to the body panels and outer cover using any of the methods of attachment described above, including for example various adhesives, stitching or other bonding methods. The absorbent composite can be secured to the body panels with any configuration of attachment lines, swirls, patterns, spots, etc., or can be a full and continuous attachment therebetween.

Referring to FIGS. 2–4, the method and apparatus for fabricating one or more embodiments of the aforedescribed refastenable absorbent garment is illustrated. Although the process is described in terms of various zones, it should be understood that it is a continuous process.

Referring to FIG. 2 at zone A1, a continuous supply or stream of absorbent garment subassemblies 300 is moved in a machine direction. The continuous absorbent garment assembly includes a continuous front body panel web 302 and a continuous rear body panel web 304. A plurality of crotch portions 306, which are formed in part by the absorbent composite 50, are spaced from each other along the machine direction. The crotch portions extend between are connected to the continuous front and rear body panel webs 302, 304. In one preferred embodiment, a continuous outer cover web 310 is connected to and forms part of the front and rear body panel webs 302, 304 and the crotch portion 306. Continuous elastic elements 308, 314 are applied to the front and rear body panel webs 302, 306 along the machine direction. In one embodiment, the elastic elements are applied between the front body panel liner and the outer cover web 310 and between the rear body panel liner and the outer cover 310. An adhesive can be applied between the liner and outer cover. In particular, an adhesive can be applied as a continuous adhesive layer, or intermittently as a continuous adhesive layer and a microbead adhesive layer. Alternatively, the adhesive can be applied intermittently, with ultrasonic bonds connecting the substrates in the regions between the application of adhesive. The adhesive is preferably applied intermittently only when a landing member is being applied over the area of no adhesive or the area of microbead adhesive, which areas also preferably include deadened elastic elements.

As the front and rear body panel webs 302, 304, which are preferably made of one or more of the materials described above, are moved along in the process in the machine direction, an adhesive can applied to one side of the front body panel web and a landing member can be applied thereto.

The plurality of elastic elements 308, 312 are preferably applied to the front and rear body panel webs in one or more of the configurations described above. For example, as shown in FIG. 2, the elastic elements are spaced uniformly across a substantial portion of the length (defined in the cross direction) of the webs. In one embodiment, the elastic elements are intermittently deactivated in a landing zone on the front body panel web with a timed elastic cutter, preferably by severing or chopping the elastic elements. A landing member, comprised of a landing material, is then applied to the front body panel web or the outer cover over the deactivated area or landing zone.

Figure 5:
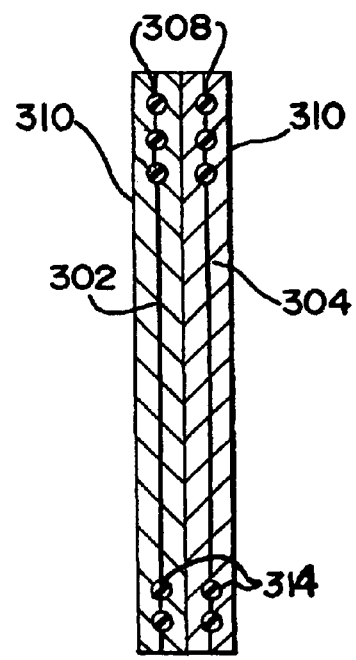
FIG. 5 is a cross-sectional view of a continuous absorbent garment subassembly taken along line 5—5 of FIG. 2.

Referring to FIG. 3, the crotch portion 306 is folded in the cross direction, thereby forming a machine direction folded edge 312, such that the front body panel web is facing the rear body panel web, and preferably with the two body panel webs 302, 304 in contact, as shown in FIG. 5. The crotch portion 306 can be folded such that the front body panel web underlies or overlies the rear body panel web, or the subassembly can be oriented in the substantially vertical direction.

Referring to FIG. 3 (zone A-1), the outer cover web 310 is successively cut to form a leg cut-out between the plurality of absorbent composites 50, and the retention portion 70 forming a part thereof. Preferably the outer cover web is cut with a die cutter before the stream of absorbent garment subassemblies is folded, although it can also be done after such folding. Alternatively, where there is no outer cover extending between the body panels, the space between the absorbent composites connecting the front and rear body panels forms the plurality of leg openings, or a die cutter can be used to further shape the body panels.

The continuous absorbent subassembly is successively cut along the cross direction, and particular, the continuous front and rear body panel webs 302, 304 are successively cut along the cross direction to form a plurality of discrete absorbent garment subassemblies 320. Each discrete absorbent garment subassembly includes a front and rear body panel 4, 6 connected with a crotch portion 312, as described above, with the cross direction cuts forming the side edges 24, 28 of each of the front and rear body panels. As the discrete absorbent garment subassemblies are formed, the side edges 24, 28 of the front and rear body panels form the leading and trailing edges of the discrete absorbent garment subassembly as it travels in the machine direction.

In one embodiment, the side edges are sealed to form the side seams in the absorbent garment. In another preferred alternative embodiment, however, the side sealing step is omitted. During the manufacturing process, the side seals can be formed for a first time period, which means the time required to make or complete a run of products having side seams. The sealing step can then be omitted for a second time period, which means the time required to make or complete a run of products that do not have side seams, but rather are "open." Of course, it should be understood that the various time periods can be reversed, or alternated to suit the needs of the manufacturer.

Instead, and referring to zone A2, the discrete absorbent garment subassemblies 320 are rotated, preferably approximately 90 degrees, such that the side edges 24, 28, which are not sealed or otherwise attached, are spaced apart in the cross direction, and such that the crotch portion 306, and in particular the folded edge 312, is the leading edge, with the waist portion forming the trailing edge in the machine direction. However, it should be understood that the orientation could be reversed 180 degrees.

Referring to FIGS. 2 and 3, the discrete absorbent garment subassemblies 320 are rotated from the machine direction to a cross direction using a product rotator 330. For example, in one embodiment, the discrete subassemblies can be rotated using an offset cam action rotator (not shown). The rotator includes a plurality of transfer segments, which can have a vacuum applied thereto, that engage the fastener members. Coupler arms connect the transfer segments and a drive ring. The coupler arm includes a cam end having a cam follower that follows the profile of a cam mechanism. The profile of the cam mechanism can be readily changed to change the desired speed output and pitch of the subassemblies. If the successive subassemblies are separated by a perforation, the transfer segment breaks the perforation as it engages the subassembly and moves away from the next subassembly, which is engaged by a next transfer segment. Alternatively, the subassemblies are already cut all of the way through, and the rotator merely moves, or separates, and rotates the subassemblies. In yet another alternative embodiment, the subassemblies are cut and separated by the transfer segments. In a preferred embodiment, the rotator rotates the end portion of the transfer segment, preferably approximately 90 degrees, about a radial axis, such that the subassemblies are oriented as described above, as the transfer segments are rotated about a horizontal axis. The rotator, and the method for the use thereof, is further disclosed in U.S. Pat. Nos. 5,761,478, 5,759,340, and 6,139,004, all of which are assigned to Kimberly-Clark Worldwide, Inc., the assignee of the present application, and all of which are hereby incorporated herein by reference.

Alternatively, the subassembly can be rotated using a revolving transfer roll rotator 330 as shown and described in U.S. Pat. No. 4,608,115, which is assigned to Kimberly-Clark Worldwide, Inc., the assignee of the present application, and which is hereby incorporated herein by reference in its entirety.

Referring to zone A3, in one embodiment, the front and rear body panels 4, 6 are separated. In particular, and referring to FIG. 3, the crotch portion an upper and lower vacuum conveyor 332, 334 that engage the garment side of the front and rear body panels 4, 6 by way of a vacuum and diverge so as to separate the front and rear body panels. The conveyors 332, 334 carry the discrete absorbent garment subassembly 320 in the machine direction until a pair of support members 336, spaced in the cross direction, engage an inner, bodyside surface of the side, ear portions 30 of the upper body panel, which is preferably the rear body panel, on each side of the conveyor. The support members 336 each have a downwardly turned or curved upstream edge or lip 338 such that the side portions 30 do not get hung up on the support members. An upper, narrow center vacuum conveyor 340 adheres to the central portion of the rear body panel 6 and moves it in the machine direction as the support members 336 elevate and support the side portions 30. The support members 336 feed the side portions 30 into a pair of fastener applicators 342, positioned on each side of the conveyor 340. The fastener applicators 342 apply a fastener member 42 to the side portion 30 on each side of the discrete absorbent garment as shown in FIG. 3 and in zone A4 of FIG. 2.

The fastener member 42 is preferably made from a strip of fastener material having a carrier material forming outer lateral base portions and a engagement material disposed along a middle portion of the carrier material to form the refastenable portion. The strip of fastener material is cut along the machine direction, preferably in a serpentine cut, to form a pair of strips 110 of fastener material, each having a plurality of tab members 47 facing laterally inward toward the other strip of fastener material. The strips of fastener material are separated and rotated or flipped about an axis parallel to the machine direction such that they are laterally spaced in the cross direction and can be fed into the cross direction spaced fastener applicators with the tab members 47 facing laterally outboard away from the other strip of fastener material. Alternatively, the fastener strips can be crossed over each other such that the tab members on each strip are facing laterally outward relative to each other. Of course, the fastener members could be oriented in the opposite direction. The strips 110 are also aligned, with one or both of the strips being moved in the machine direction relative to the other, such that the tab members 47 are aligned in the cross direction opposite each other. For example, U.S. Pat. No. 5,540,796, entitled Process for Assembling Elasticized Ear Portions and assigned to Kimberly-Clark Corporation, the entire disclosure of which is hereby incorporated herein by reference, discloses one way of cutting, separating, and aligning fastener members.

The fastener applicators 342 cut the strips 110 of fastener material to form a plurality of fastener members 42 and secures the base portion 55 of the fastener members 42 to the side portions 30 of the rear body panel 6, preferably with an adhesive. As the side portions 30, with a fastener member 42 now attached thereto, leave the fastener applicator 342, a pair of second support members 348 again support the side portions 30 and introduce the side portions 30, with the fastener members 42 attached thereto, into a pair of bonders 350 positioned on each side of the conveyor 340. The bonders 350, which can include a nip, further bonds the fastener member to the body panel the fastener members. Preferably, the fastener members are bonded to the body panel with one or more, and preferably two, ultrasonic bonders 620. Exemplary ultrasonic bonders are disclosed in U.S. Pat. Nos. 6,123,792 and 5,660,679, the entire disclosures of which are hereby incorporated by reference. Of course, it should be understood that the fastener members can be secured to the body panel with adhesive bonds, thermal bonds, stitching and other types of attachment known to those of skill in the art.

The fastener member 42 can then be folded over on the rear body panel 6 as shown in FIG. 1, and the finished absorbent garment can be further folded and packaged for delivery for sale to the end user.

In an alternative embodiment, the front and rear body panels are not separated. Rather, the fastener members are attached to the garment side of the side portions of one or both of the front and rear body panels. For example, the fastener members can be self adhered, for example by gluing, to the garment side of the side portions of one or both of the front or rear body panel. Alternatively, the base portion of the fastener members can be attached to the body panel with a mechanical type fastener, for example a hook and loop type fastener.

In addition, the side edges of the front and rear body panels can be bonded to form a side seam as explained above, with the fastener member secured to one or both of the front and rear body panels. Preferably, the front body panel also includes longitudinally extending lines of weakness, which can be broken by the user. For example, the lines of weakness can be formed as longitudinally extending perforations on the front body panel. The perforations, or other lines of weakness, can be formed in the cross direction before the subassembly is folded, cut, and rotated or they can be made in the machine direction after the subassembly is folded, cut and rotated as the front and rear body panels are separated. Preferably, the fastener member bridges the line of weakness and engages the front body panel, or any landing member disposed thereon, inboard of the line of weakness.

Various aspects of the process for making the absorbent garment are further disclosed in U.S. application Ser. No. 09/834,870, filed Apr. 13, 2001, and entitled "Multiple Component Web," U.S. application Ser. No. 09/834,875, filed Apr. 13, 2001 and entitled "Method of Assembling Personal Care Absorbent Article," U.S. application Ser. No. 09/834,869, filed Apr. 13, 2001, and entitled "Pant-Type Personal Care Articles, and Methods of Making and Using Such Personal Care Articles," U.S. application Ser. No. 09/834,787, filed Apr. 13, 2001 and entitled "Methods of Changing Size of Pant-Type Personal Care Articles Outputted from a Manufacturing Process," and U.S. application Ser. No. 09/834,682, filed Apr. 13, 2001 and entitled "Passive Bonds For Personal Care Article," the entire disclosures of which are hereby incorporated by reference.

In other aspects, the absorbent garment and the process for making the absorbent garment are further disclosed in U.S. Provisional Application Ser. No. 60/303,307, filed Jul. 5, 2001, and entitled "Refastenable Absorbent Garment," the entire disclosure of which is hereby incorporated by reference.

Although the present invention has been described with reference to preferred embodiments, those skilled in the art will recognize that changes may be made in form and detail without departing from the spirit and scope of the invention. As such, it is intended that the foregoing detailed description be regarded as illustrative rather than limiting and that it is the appended claims, including all equivalents thereof, which are intended to define the scope of the invention.

What is claimed is:

1. A method for manufacturing a refastenable absorbent garment comprising:

moving a continuous absorbent garment subassembly in a machine direction, wherein said continuous absorbent garment subassembly comprises a continuous front body panel web, a continuous rear body panel web and a plurality of discrete crotch portions spaced along said machine direction and extending between said continuous front and rear body panel webs, wherein said crotch portions are folded in a cross direction with one of said continuous front and rear body panel webs facing the other of said continuous front and rear body panel webs;

successively cutting said continuous front and rear body panels of said continuous absorbent garment subassembly in said cross direction and thereby forming a plurality of discrete absorbent garment subassemblies comprising a front body panel and a rear body panel, wherein said front and rear body panels are connected with said crotch portion, each of said front and rear body panels having opposite side edges, wherein said side edges form leading and trailing edges of said discrete absorbent garment subassemblies in the machine direction;

successively rotating each of said discrete absorbent garment subassemblies such that said side edges are spaced apart in said cross direction; and attaching a fastener member to at least one of said front and rear body panels on each of said discrete absorbent garment subassemblies.

2. The invention of claim 1 further comprising moving a fastener material in a machine direction and cutting said fastener material to form said fastener members.

3. The invention of claim 2 wherein said moving said fastener material in said machine direction comprises moving at least two strips of said fastener material in a spaced apart relationship in said machine direction.

4. The invention of claim 3 wherein said moving at least said two strips of said fastener material comprises moving a web of fastener material having a middle portion comprising a refastenable portion and outer lateral portions comprising a base portion, and further comprising cutting said middle portion along said machine direction and thereby forming said at least said two strips of said fastener material and separating said at least said two strips in said cross direction to form said spaced apart relationship therebetween, and wherein said attaching a fastener member to said at least said one of said front and rear body panels on each of said discrete absorbent garment subassemblies comprises attaching said base portions of said strips to said at least said one of said front and rear body panels on each of said discrete absorbent garment subassemblies.

5. The invention of claim 4 wherein said cutting said middle portion along said machine direction comprises making a serpentine cut along said middle portion and thereby forming a plurality of tabs forming said refastenable portions of said at least two strips of fastener material.

6. The invention of claim 1 wherein said attaching a fastener member to at least one of said front and rear body panels on each of said discrete absorbent garment subassemblies comprises attaching said fastener member adjacent said side edges of said at least one of said front and rear body panels on each of said discrete absorbent garment subassemblies.

7. The invention of claim 1 wherein said front body panel web comprises a landing member.

8. The invention of claim 7 wherein said landing member comprises a point-unbonded material.

9. The invention of claim 1 wherein said fastener member comprises a refastenable portion.

10. The invention of claim 9 wherein said refastenable portion comprises a hook-type fastener material.

11. The invention of claim 9 wherein said refastenable portion comprises an adhesive tape material.

12. The invention of claim 1 further comprising an outer cover forming in part said crotch portion and said front and rear body panel webs.

13. The invention of claim 12 wherein said crotch portion comprises a retention portion.

14. The invention of claim 12 further comprising successively cutting said outer cover between said retention portions and thereby forming leg openings.

15. The invention of claim 13 wherein at least one of said front and rear body panel webs comprises a plurality of elastic strands running along said machine direction.

16. The invention of claim 15 further comprising deactivating said plurality of said elastic strands in successively spaced landing zones.

17. The invention of claim 1 wherein said fastener member comprises a carrier member.

18. The invention of claim 17 wherein said carrier member is elasticized.

19. The invention of claim 1 wherein a bodyside surface of each of said front and rear body panels are in contact, and further comprising separating said front and rear body panels prior to said attaching said fastener member to said at least said one of said front and rear body panels.

20. The invention of claim 19 further comprising bringing said bodyside surface of said front and rear body panels into contact after attaching said fastener member to said to said at least said one of said front and rear body panels.

21. The invention of claim 1 wherein said attaching said fastener member to said to said at least said one of said front and rear body panels comprises bonding said fastener member to said at least one of said front and rear body panels.

22. The invention of claim 1 wherein said attaching said fastener member to said to said at least said one of said front and rear body panels comprises attaching a pair of fastener members to said rear body panel.

23. The invention of claim 22 wherein said attaching a pair of fastener members to said rear body panel comprises attaching said pair of fastener members to a garment side surface of said rear body panel.

24. The invention of claim 1 said fastener member comprises a plurality of first fastener members having a first width and a plurality of second fastener members having a second width, wherein said second width is different than said first width, and wherein said attaching said fastener member to said at least one of said front and rear body panels on said each of said discrete absorbent garment subassemblies comprises successively attaching said plurality of said first fastener members to said at least one of said front and rear body panels on said each of said discrete absorbent garment subassemblies and then successively attaching said plurality of said second fastener member to said at least one of said front and rear body panels on said each of said discrete absorbent garment subassemblies.

25. An apparatus for fabricating a refastenable absorbent garment comprising a front and rear body panel connected by a crotch portion, wherein the crotch portion is folded with one of the front and rear body panel overlying the other of the front and rear body panel, the apparatus comprising:
   a product rotator adapted to rotate the absorbent garment from a cross direction to a machine direction;
   at least one vacuum conveyor positioned downstream of said product rotator and adapted to separate the front and rear body panels; and
   a fastener applicator positioned downstream of said at least one vacuum conveyor and adapted to apply a fastener member to at least one of the front and rear body panels.

26. The invention of claim 25 further comprising a support member positioned on at least one side of said at least one vacuum conveyor and adapted to support a side portion of at least one of said front and rear body panels.

27. The invention of claim 25 comprising a pair of tab applicators positioned on opposite sides of said at least one vacuum conveyor.

28. The invention of claim 25 wherein said at least one vacuum conveyor comprises at least one an upper and lower vacuum conveyor, each of which is adapted to support one of said front and rear body panels.

29. The invention of claim 25 further comprising a bonder positioned downstream of said fastener applicator.

30. The invention of claim 29 wherein said bonder comprises a pair of ultrasonic bonders positioned on opposite sides of said at least one vacuum conveyor.

31. A method for manufacturing absorbent garments comprising:
   moving a continuous absorbent garment subassembly in a machine direction, wherein said continuous absorbent garment subassembly comprises a continuous front body panel web, a continuous rear body panel web and a plurality of discrete crotch portions spaced along said machine direction and extending between said continuous front and rear body panel webs, wherein said crotch portions are folded in a cross direction with one of said continuous front and rear body panel webs facing the other of said continuous front and rear body panel webs;

successively sealing said front and rear body panel webs along said cross direction and thereby forming a plurality of cross direction side seams spaced along said machine direction for a first time period;

discontinuing said sealing for a second time period;

successively cutting said continuous front and rear body panels of said continuous absorbent garment subassembly in said cross direction and thereby forming a plurality of discrete absorbent garment subassemblies comprising a front body panel and a rear body panel, wherein said front and rear body panels are connected with said crotch portion, each of said front and rear body panels having opposite side edges, wherein said side edges form leading and trailing edges of said discrete absorbent garment subassemblies in the machine direction;

successively rotating each of said discrete absorbent garments such that said side edges are spaced apart in said cross direction; and attaching a fastener member to at least one of said front and rear body panels on each of said discrete absorbent garment subassemblies fabricated during at least said second time period.

* * * * *